(12) United States Patent
Kreimerman et al.

(10) Patent No.: US 11,572,333 B2
(45) Date of Patent: Feb. 7, 2023

(54) PROCESSES FOR THE PRODUCTION OF ISOMERICALLY PURE OR ENRICHED CIS-CLOMIPHENE

(71) Applicant: PCAS, Ecully (FR)

(72) Inventors: Sergio Kreimerman, Porcheville (FR); Sandrine Gauthier, Breuilpont (FR); Quentin Llopis, Paris (FR)

(73) Assignee: PCAS, Ecully (FR)

( * ) Notice: Subject to any disclaimer, the term of this patent is extended or adjusted under 35 U.S.C. 154(b) by 0 days.

(21) Appl. No.: 17/302,441

(22) Filed: May 3, 2021

(65) Prior Publication Data
US 2021/0340096 A1 Nov. 4, 2021

(30) Foreign Application Priority Data
May 4, 2020 (EP) .................................... 20305433

(51) Int. Cl.
C07C 213/08 (2006.01)
(52) U.S. Cl.
CPC ........ C07C 213/08 (2013.01); *C07B 2200/07* (2013.01); *C07B 2200/13* (2013.01)
(58) Field of Classification Search
None
See application file for complete search history.

(56) References Cited

U.S. PATENT DOCUMENTS

| 2,914,563 | A | 11/1959 | Allen et al. |
| 3,848,030 | A | 11/1974 | Viterbo et al. |
| 4,061,733 | A | 12/1977 | Gunjikar |
| 5,565,611 | A | 10/1996 | Fumihiko et al. |

FOREIGN PATENT DOCUMENTS

| FR | 3082842 A1 | 12/2019 |
| WO | WO-2014/031177 A1 | 2/2014 |
| WO | WO-2015/138340 A1 | 9/2015 |

OTHER PUBLICATIONS

International Search Report and Written Opinion, corresponding International Application No. PCT/EP2021/061570, dated Jul. 8, 2021.
Extended European Search Report, for European Patent Application No. 20305433.3, dated Oct. 27, 2020.
E. M. Dolginova et al., "Synthesis and biological study of the cis- and tran-sisomers of clomiphene citrate and some intermediates of its synthesis" Pharmaceutical Chemistry Journal, vol. 18. No. 11, Nov. 1, 1984, pp. 758-764.

*Primary Examiner* — Sudhakar Katakam
*Assistant Examiner* — Jennifer C Sawyer
(74) *Attorney, Agent, or Firm* — Marshall, Gerstein & Borun LLP

(57) ABSTRACT

The present disclosure relates to methods for the production of the isomerically pure or isomerically enriched cis-clomiphene and salts thereof.

17 Claims, No Drawings

PROCESSES FOR THE PRODUCTION OF ISOMERICALLY PURE OR ENRICHED CIS-CLOMIPHENE

CROSS-REFERENCE TO RELATED APPLICATION

The present application claims the benefit of priority to European Patent Application No. 20305433.3, filed May 4, 2020, which is hereby incorporated herein by reference.

The present invention relates to methods for the production of the isomerically pure or isomerically enriched cis-clomiphene and salts thereof.

BACKGROUND OF THE INVENTION

Clomiphene is an active pharmaceutical ingredient currently approved for treating ovulatory dysfunction, in particular for inducing ovulation in anovulatory women. Clomiphene is a mixture of two geometric isomers, trans-clomiphene (or enclomiphene or isomer E) and cis-clomiphene (or zuclomiphene or isomer Z). Commercially available medicine form of clomiphene is clomiphene citrate containing about 70% of trans-clomiphene.

In the past decades, efforts were spent in developing methods for synthesizing clomiphene and isolating the pure trans-isomer known to be a selective estrogen receptor modulator (U.S. Pat. No. 2,914,563; WO2014/031177; WO2015/138340). Not much attention was paid to the preparation and isolation of the cis-isomer. However, interest in the cis-isomer is growing as zuclomiphene is currently ongoing clinical development for new clinical applications. As a consequence, the need for cost efficient processes for the preparation of zuclomiphene at industrial scale becomes stronger.

Few methods for isolating the two isomers are known. For instance, U.S. Pat. No. 3,848,030 describes the resolution of clomiphene geometric isomers using racemic binaphthyl-phosphoric acid (BPA). U.S. Pat. No. 4,061,733 discloses fractional crystallization of clomiphene by refluxing clomiphene in carbon disulfide in a reflux condenser. However, none of these methods are suitable for producing zuclomiphene at industrial scale, these methods being laborious and costly.

In the absence of reported industrial processes for producing zuclomiphene, the need remains to provide efficient processes for providing pure cis-clomiphene at industrial scale.

SUMMARY OF THE INVENTION

The invention relates to a process for the production of isomerically enriched cis-clomiphene free base or a salt thereof from isomerically pure or isomerically enriched trans-clomiphene hydrobromide comprising the steps of:

(a) reacting hydrobromic acid with the isomerically pure or isomerically enriched trans-clomiphene hydrobromide in the absence of organic solvent to provide isomerically enriched cis-clomiphene hydrobromide, and (b) optionally converting the isomerically enriched cis-clomiphene hydrobromide to isomerically enriched cis-clomiphene free base or a salt thereof other than hydrobromide.

The invention further relates to process for selectively crystallizing isomerically pure cis-clomiphene hydrobromide from a mixture of trans- and cis-clomiphene free base which comprises the step of reacting hydrobromic acid with the mixture of trans- and cis-clomiphene free base in acetone, wherein the mixture of trans- and cis-clomiphene free base comprises at least 40 wt. % of cis-clomiphene free base relative to the total weight of the mixture of trans- and cis-clomiphene free base.

The invention further relates to a process for preparing isomerically pure cis-clomiphene free base or a salt thereof comprising the steps of:

(a) reacting hydrobromic acid with isomerically pure or isomerically enriched trans-clomiphene hydrobromide in the absence of organic solvent to provide isomerically enriched cis-clomiphene hydrobromide;

(b) converting the isomerically enriched cis-clomiphene hydrobromide obtained in step (a) to an isomerically enriched cis-clomiphene free base;

(c) reacting hydrobromic acid with the isomerically enriched cis-clomiphene free base obtained in step (b) in acetone to selectively crystallize isomerically pure cis-clomiphene hydrobromide;

(d) optionally converting the isomerically pure cis-clomiphene hydrobromide obtained in step (c) to isomerically pure cis-clomiphene free base;

(e) optionally converting the isomerically pure cis-clomiphene hydrobromide obtained in step (c) or the isomerically pure cis-clomiphene free base obtained in step (d) to an isomerically pure cis-clomiphene salt other than the isomerically pure cis-clomiphene hydrobromide.

The invention further relates to processes for preparing cis-clomiphene citrate as crystalline form I or VI, which comprises respectively the step of crystallizing cis-clomiphene citrate in acetone or the step of crystallizing cis-clomiphene citrate in a solvent selected from the group consisting of butan-2-ol, methanol, isopropyl alcohol and methyl tert-butyl ether or in a mixture acetone/water.

The invention further relates to a process for converting crystalline form I of cis-clomiphene citrate to crystalline form VI of cis-clomiphene citrate which comprises the step of adding crystalline form I of cis-clomiphene citrate in a mixture consisting of acetone and water in order to obtain a slurry, heating the slurry at a temperature ranging from about 40 to 55° C. and collecting cis-clomiphene citrate as crystalline form VI.

Definitions

The term "clomiphene" as used herein designates 2-[4-(2-chloro-1,2-diphenylethenyl)phenoxy]-N,N-diethyl-ethanamine (Cas No. [911-45-5]) in its free base form as a mixture of cis- and trans isomers.

The term "cis-clomiphene" as used herein designates 2-[4-((Z)-2-chloro-1,2-diphenylethenyl)phenoxy]-N,N-diethylethanamine in its free base form.

The term "trans-clomiphene" as used herein designates 2-[4-((E)-2-chloro-1,2-diphenylethenyl)phenoxy]-N,N-diethylethanamine in its free base form.

The term "isomerically pure" as used herein with reference to a compound comprising two isomers shall mean that one isomer is present in an amount of at least 95%, preferably at least 98%, preferably at least 99% relative to the total amount of compound, i.e. the isomeric ratio cis to trans or trans to cis is equal to or larger than 95:5, preferably equal to or larger than 98:2, preferably equal to or larger than 99:1. An isomerically pure compound may comprise up to 100% of one isomer relative to the total amount of compound (cis and trans isomers). Percents are expressed as wt. % or mol. %.

The term "isomerically pure cis-clomiphene" as used herein shall mean that cis-clomiphene is present in an amount of at least 95%, preferably at least 98%, preferably at least 99% relative to the total amount of cis- and trans-clomiphene, i.e. the isomeric ratio cis-clomiphene to trans-clomiphene is equal to or larger than 95:5, preferably equal to or larger than 98:2, preferably equal to or larger than 99:1. Isomerically pure cis-clomiphene may comprise up to 100% of cis-clomiphene relative to the total amount of compound (cis- and trans-clomiphene). Percents are expressed as wt. % or mol. %.

The term "isomerically enriched" as used herein with reference to a compound shall designate a mixture of cis and trans isomers of said compound in which one of the isomers is preponderant, i.e. the isomeric ratio cis to trans or trans to cis is larger than 50:50 but lower than 95:5.

The term "isomerically enriched cis-clomiphene" as used herein shall designate a mixture of cis- and trans-clomiphene in which cis-clomiphene is preponderant, i.e. the isomeric ratio cis-clomiphene to trans-clomiphene is larger than 50:50 but lower than 95:5.

The term "mixture of isomers" as used herein shall encompass mixtures with an isomeric ratio of 50:50 and isomerically enriched mixtures.

The term "pharmaceutically acceptable salt" as used herein shall designate a salt of a compound which is generally safe and non-toxic for a pharmaceutical use.

The term "about" means in the context of the present invention that the concerned value may be lower or higher by 10% (±0.1), especially by 5% (±0.05), in particular by 1% (±0.01), than the value indicated.

Percentage by weight, percentage by moles and percentage by volume are respectively abbreviated herein as wt. %, mol. % and vol. %.

DESCRIPTION OF THE INVENTION

It is an object of the present invention to provide efficient processes for preparation of isomerically enriched cis-clomiphene and/or for preparation of isomerically pure cis-clomiphene which work reliably even on large scale.

Production of Isomerically Enriched Cis-Clomiphene

The present invention relates to a process for the production of isomerically enriched cis-clomiphene or a salt thereof from isomerically pure or isomerically enriched trans-clomiphene hydrobromide.

The process for the production of isomerically enriched cis-clomiphene or a salt thereof from isomerically pure or isomerically enriched trans-clomiphene hydrobromide comprises the step of reacting hydrobromic acid with isomerically pure or isomerically enriched trans-clomiphene hydrobromide in the absence of organic solvent. It was surprisingly found that reacting hydrobromic acid with isomerically pure or isomerically enriched trans-clomiphene hydrobromide in the absence of organic solvent allows isomerization of clomiphene hydrobromide.

The starting materials, i.e. isomerically pure or isomerically enriched trans-clomiphene hydrobromide, for the preparation of isomerically enriched cis-clomiphene or a salt thereof can be readily obtained by conventional synthesis methods, for example as described in U.S. Pat. No. 2,914,563, or can be obtained commercially. In isomerically enriched trans-clomiphene hydrobromide, the ratio of the trans isomer to the cis isomer may vary freely. In some embodiments, the ratio of the trans isomer to the cis isomer ranges from 70:30 to 75:25.

The hydrobromic acid is typically in the form of an aqueous solution. The concentration of hydrobromic acid in the aqueous solution is not specifically limited, but is generally of about 48 wt. %. The hydrobromic acid is typically used in excess with respect to the isomerically pure or isomerically enriched trans-clomiphene hydrobromide. In some embodiments, at least four volumes, typically from four to ten volumes of hydrobromic acid 48 wt %, preferably four volumes, are reacted with isomerically pure or isomerically enriched trans-clomiphene hydrobromide. One volume means 1 mL per 1 gram of isomerically pure or isomerically enriched trans-clomiphene hydrobromide.

The reaction of hydrobromic acid with isomerically pure or isomerically enriched trans-clomiphene hydrobromide is typically performed at a temperature ranging from about 45° C. to about 80° C., preferably at about 70° C. The mixture is maintained at the same temperature until the end of the reaction.

The reaction of hydrobromic acid with isomerically pure or isomerically enriched trans-clomiphene hydrobromide is typically conducted until the ratio of cis clomiphene to trans clomiphene is larger than 50:50. The progress of the conversion is typically monitored by HPLC. The process according to the present invention allows obtaining isomerically enriched cis-clomiphene hydrobromide wherein the ratio of cis-clomiphene to trans-clomiphene typically ranges from larger than 50:50 to about 55:45. In some embodiments, the ratio of cis-clomiphene to trans-clomiphene ranges from larger than 50:50 to about 52:48.

The process for the production of isomerically enriched cis-clomiphene or a salt thereof may further comprise the step of converting the isomerically enriched cis-clomiphene hydrobromide resulting from the above-described step to isomerically enriched cis-clomiphene free base. The conversion to the free base may be performed directly on the slurry obtained in the previous disclosed step, i.e. no purification and isolation is needed, typically after the slurry has been cooled down to room temperature, i.e. 20 to 25° C. The conversion to the free base may be performed by conventional methods.

In some embodiments, the conversion to the free base comprises reacting the isomerically enriched cis-clomiphene hydrobromide with a base. Suitable base includes alkaline metal hydroxide (e.g. sodium hydroxide), sodium bicarbonate and the like. Typically, the isomerically enriched cis-clomiphene hydrobromide is reacted with about 1 equivalent of base, e.g. sodium hydroxide, relative to the hydrobromic acid. The base is typically in the form of an aqueous solution. The concentration of base in the aqueous solution is not specifically limited. Conveniently, a solution of sodium hydroxide 5M may be used. The base is generally added gradually at room temperature, i.e. 20° C. to 25° C., to the isomerically enriched cis-clomiphene hydrobromide. The base may be gradually added over a period of 10 minutes to 120 minutes. In some embodiments, the period ranges from 45 to 75 minutes. In some embodiments, the period is about 60 minutes.

The isomerically enriched cis-clomiphene free base may be then isolated by any suitable known conventional methods, such as by extraction with a suitable water immiscible solvent, for instance with ethyl acetate, and concentration.

The process according to the present invention allows obtaining isomerically enriched cis-clomiphene free base wherein the ratio of cis-clomiphene to trans-clomiphene ranges preferably from larger than 50:50 to about 55:45. In some embodiments, the ratio of cis-clomiphene to trans-clomiphene ranges from larger than 50:50 to about 52:48.

The isomerically enriched cis-clomiphene free base may be further converted to any salt, preferably to any suitable pharmaceutically acceptable acid salt. Conversion may be performed by conventional methods. Examples of pharmaceutically acceptable acid salts include addition salts with inorganic acid, such as hydrochloric, hydrobromic, sulfuric, nitric and phosphoric acid and the like or with organic acid, such as citric, oxalic, formic, acetic, benzenesulfonic, fumaric, glucoheptonic, gluconic, glutamic, glycolic, hydroxynaphthoic, 2-hydroxyethanesulfonic, lactic, maleic, malic, mandelic, methanesulfonic, muconic, 2-naphthalenesulfonic, propionic, succinic, dibenzoyl-L-tartaric, tartaric, p-toluenesulfonic, trimethylacetic, and trifluoroacetic acid and the like.

Selective Crystallization of Cis-Clomiphene Hydrobromide

Selective crystallization of cis-clomiphene or a salt thereof has appeared to be challenging since attempts to selectively crystallize cis-clomiphene starting with the citrate salt or in accordance with suggested procedures, such as disclosed in U.S. Pat. No. 5,565,611, has failed. However, it was surprisingly found that selective crystallization of cis-clomiphene may be achieved via the preparation of clomiphene hydrobromide in acetone, when starting with a mixture of trans- and cis-clomiphene free base comprising at least 40 wt. % of cis-clomiphene free base relative to the total weight of the mixture of trans- and cis-clomiphene free base, thus allowing isolation of the isomerically pure cis-clomiphene.

Hence, the present invention also relates to a process for selectively crystallizing isomerically pure cis-clomiphene hydrobromide from a mixture of trans- and cis-clomiphene free base which comprises the step of reacting hydrobromic acid with the mixture of trans- and cis-clomiphene free base in acetone, wherein the mixture of trans- and cis-clomiphene free base comprises at least 40 wt. % of cis-clomiphene free base relative to the total weight of the mixture of trans- and cis-clomiphene free base.

The amount of cis-clomiphene free base in the mixture may vary greatly. In some embodiments, the mixture of trans- and cis-clomiphene free base comprises at least 45 wt. %, preferably at least 50 wt. % of cis-clomiphene free base relative to the total weight of the mixture. Attempts to selectively crystallize cis-clomiphene hydrobromide in mixtures comprising a lower amount of cis-clomiphene free based were unsuccessful. The mixture may comprise up to 95 wt. % of cis-clomiphene free base relative to the total weight of the mixture.

In some embodiments, the mixture of trans- and cis-clomiphene free base is an isomerically enriched cis-clomiphene free base, which may be prepared in accordance with the process disclosed herein. In some embodiments, the mixture of trans- and cis-clomiphene free base comprises from about 50 wt. % to 55 wt. % of cis-clomiphene free base relative to the total weight of the mixture.

The hydrobromic acid is typically in the form of an aqueous solution. The concentration of hydrobromic acid in the aqueous solution is not specifically limited, but is generally of about 48 wt. %. The hydrobromic acid is typically used in an amount ranging from 0.9 to 1.2 equivalents, typically from 1 to 1.1 equivalents, preferably in an equimolar amount, relative to the mixture of trans- and cis-clomiphene free base. Hydrobromic acid is typically added gradually to the mixture of trans- and cis-clomiphene free base, preferably at room temperature, i.e. 20° C. to 25° C. Hydrobromic acid may be gradually added over a period of 10 minutes to 60 minutes. In some embodiments, the period is about 30 minutes.

Once the hydrobromic acid addition is completed, the slurry is then typically heated to a temperature lower than the boiling point of acetone, typically at a temperature ranging from about 45 to about 50° C., preferably at about 50° C. The slurry, which may be seeded with isomerically pure cis-clomiphene, is then allowed to cool to room temperature, i.e. 20° C. to 25° C., thereby causing cis-clomiphene hydrobromide to crystallize.

The precipitated cis-clomiphene hydrobromide is then isolated. Isolation may be performed by any conventional means, such as by filtration or centrifugation. The isolated cis-clomiphene hydrobromide may then be washed and dried.

The cis-clomiphene hydrobromide obtained by the process of the invention has a high isomeric purity. The isomeric ratio cis-clomiphene to trans-clomiphene is at least 95:5. The isomeric ratio cis-clomiphene to trans-clomiphene is typically equal to or larger than 95:5, preferably equal to or larger than 98:2. The isomeric ratio cis-clomiphene to trans-clomiphene may be up to 100:0 or up to 99.9:0.1 or up to 99.5:0.5. In other words, the product obtained by the process of the invention comprises at least 95 wt. % or at least 98 wt. % of cis-clomiphene hydrobromide and may comprise up to 100 wt. % or up to 99.9 wt. % or up to 99.5 wt. % of cis-clomiphene hydrobromide relative to the total amount of cis- and trans-clomiphene.

The isomerically pure cis-clomiphene hydrobromide may be further converted to the free base and/or to any suitable pharmaceutically acceptable acid salt of high isomeric purity. Conversion may be performed by conventional methods. Examples of pharmaceutically acceptable acid salts include addition salts with inorganic acid, such as hydrochloric, hydrobromic, sulfuric, nitric and phosphoric acid and the like or with organic acid, such as citric, oxalic, formic, acetic, benzenesulfonic, fumaric, glucoheptonic, gluconic, glutamic, glycolic, hydroxynaphthoic, 2-hydroxyethanesulfonic, lactic, maleic, malic, mandelic, methanesulfonic, muconic, 2-naphthalenesulfonic, propionic, succinic, dibenzoyl-L-tartaric, tartaric, p-toluenesulfonic, trimethylacetic, and trifluoroacetic acid and the like.

Preparation of Isomerically Pure Cis-Clomiphene Free Base or a Salt Thereof

The present invention also relates to a process for preparing isomerically pure cis-clomiphene free base or a salt thereof comprising the steps of:

(a) reacting hydrobromic acid with isomerically pure or isomerically enriched trans-clomiphene hydrobromide in the absence of organic solvent to provide isomerically enriched cis-clomiphene hydrobromide;

(b) converting the isomerically enriched cis-clomiphene hydrobromide obtained in step (a) to an isomerically enriched cis-clomiphene free base;

(c) reacting hydrobromic acid with the isomerically enriched cis-clomiphene free base obtained in step (b) in acetone to selectively crystallize isomerically pure cis-clomiphene hydrobromide;

(d) optionally converting the isomerically pure cis-clomiphene hydrobromide obtained in step (c) to isomerically pure cis-clomiphene free base;

(e) optionally converting the isomerically pure cis-clomiphene hydrobromide obtained in step (c) or the isomerically pure cis-clomiphene free base obtained in step (d) to an isomerically pure cis-clomiphene salt other than the isomerically pure cis-clomiphene hydrobromide.

Preparation of Isomerically Pure Cis-Clomiphene Hydrobromide

The present invention also relates to a process for preparing isomerically pure cis-clomiphene hydrobromide comprising the steps of:

(a) reacting hydrobromic acid with isomerically pure or isomerically enriched trans-clomiphene hydrobromide in the absence of organic solvent to provide isomerically enriched cis-clomiphene hydrobromide;

(b) converting the isomerically enriched cis-clomiphene hydrobromide obtained in step (a) to an isomerically enriched cis-clomiphene free base;

(c) reacting hydrobromic acid with isomerically enriched cis-clomiphene free base obtained in step (b) in acetone to selectively crystallize isomerically pure cis-clomiphene hydrobromide.

Steps (a) and (b) may be performed as disclosed herein above in the section "Production of isomerically enriched cis-clomiphene".

Step (c) may be performed as disclosed herein above in the section "Selective crystallization of cis-clomiphene hydrobromide".

The isomerically pure cis-clomiphene hydrobromide can then be converted to free base or to any pharmaceutically acceptable acid salt by any conventional methods. Examples of pharmaceutically acceptable acid salts include addition salts with inorganic acid, such as hydrochloric, hydrobromic, sulfuric, nitric and phosphoric acid and the like or with organic acid, such as citric, oxalic, formic, acetic, benzenesulfonic, fumaric, glucoheptonic, gluconic, glutamic, glycolic, hydroxynaphthoic, 2-hydroxyethanesulfonic, lactic, maleic, malic, mandelic, methanesulfonic, muconic, 2-naphthalenesulfonic, propionic, succinic, dibenzoyl-L-tartaric, tartaric, p-toluenesulfonic, trimethylacetic, and trifluoroacetic acid and the like.

Preparation of Isomerically Pure Cis-Clomiphene Citrate

The present invention also relates to a process for preparing isomerically pure cis-clomiphene citrate comprising the steps of:

(a) reacting hydrobromic acid with isomerically pure or isomerically enriched trans-clomiphene hydrobromide in the absence of organic solvent to provide isomerically enriched cis-clomiphene hydrobromide;

(b) converting the isomerically enriched cis-clomiphene hydrobromide obtained in step (a) to an isomerically enriched cis-clomiphene free base;

(c) reacting hydrobromic acid with the isomerically enriched cis-clomiphene free base obtained in step (b) in acetone to selectively crystallize isomerically pure cis-clomiphene hydrobromide;

(d) converting the isomerically pure cis-clomiphene hydrobromide obtained in step (c) in isomerically pure cis-clomiphene free base;

(e) converting the isomerically pure cis-clomiphene free base obtained in step (d) to isomerically pure cis-clomiphene citrate.

Steps (a) and (b) may be performed as disclosed herein above in the section "Production of isomerically enriched cis-clomiphene".

Step (c) may be performed as disclosed herein above in the section "Selective crystallization of cis-clomiphene hydrobromide".

Steps (d) and (e) may be performed according to methods well-known to the person skilled in the art.

In some embodiments, the conversion of the isomerically pure cis-clomiphene hydrobromide to the free base comprises reacting the isomerically pure cis-clomiphene hydrobromide with a base, preferably in a mixture comprising an organic solvent and water. An example of suitable organic solvent includes ethyl acetate. The conversion is typically performed at room temperature, i.e. 20° C. to 25° C. Suitable base includes alkaline metal hydroxide (e.g. sodium hydroxide), sodium bicarbonate and the like. Typically, at least one equimolar amount of base, e.g. sodium hydroxide, is used relative to the cis-clomiphene hydrobromide. In some embodiments, from one to four equivalents of base relative to the cis-clomiphene hydrobromide are used. In some embodiments, about 3 equivalents of base relative to the cis-clomiphene hydrobromide are used. The isomerically pure cis-clomiphene free base may be then isolated by any suitable conventional methods known, such as by phase separation and extraction with a suitable water immiscible solvent, for instance with ethyl acetate, and concentration.

In some embodiments, the conversion of the isomerically pure cis-clomiphene free base to isomerically pure cis-clomiphene citrate is performed by reacting citric acid with isomerically pure cis-clomiphene free base, preferably in an organic solvent, such as acetone. Citric acid is typically added gradually to the slurry, preferably at a temperature below the boiling point of the organic solvent, typically at a temperature ranging from about 45° C. to about 50° C., preferably at about 50° C. Citric acid may be gradually added over a period of 30 minutes to 6 hours. In some embodiments, the period is about 5 hours. The slurry, which may be seeded with isomerically pure cis-clomiphene citrate, is then allowed to cool to room temperature, i.e. 20° C. to 25° C., thereby causing isomerically pure cis-clomiphene citrate to crystallize and precipitate.

The precipitated isomerically pure cis-clomiphene citrate may be then isolated. Isolation may be performed by any conventional means, such as by filtration or centrifugation. The isolated isomerically pure cis-clomiphene citrate may then be washed and dried.

The cis-clomiphene citrate obtained by the process of the invention has a high isomeric purity. The isomeric ratio cis-clomiphene citrate to trans-clomiphene citrate is at least 95:5. The isomeric ratio cis-clomiphene citrate to trans-clomiphene citrate is typically larger than 95:5, preferably equal to or larger than 98:2, even equal to or larger than 99:1. The isomeric ratio cis-clomiphene citrate to trans-clomiphene citrate may be up to 100:0 or up to 99.9:0.1 or up to 99.5:0.5. In other words, the product obtained by the process of the invention comprises at least 95 wt. % or at least 98 wt. % or at least 99 wt. % of cis-clomiphene citrate and may comprise up to 100 wt. % or up to 99.9 wt. % or up to 99.5 wt. % of cis-clomiphene citrate relative to the total amount of cis- and trans-clomiphene.

Polymorphic forms I and VI of cis-clomiphene citrate have been described (FR 3 082 842). As it is well known in the art, polymorphism is the ability of a solid compound to crystallize in more than one form or crystal structure. Crystal engineering is of importance in the production of active pharmaceutical ingredients. Polymorphic forms I and VI of cis-clomiphene are characterized by distinct XRPD patterns and melting point.

It has been found that crystallization of isomerically pure cis-clomiphene citrate in acetone (as described above in connection with step (e)) allows preparing cis-clomiphene citrate as crystalline form I whereas crystallization (or recrystallisation) of isomerically pure cis-clomiphene citrate in a solvent selected from the group of butan-2-ol, methanol, isopropyl alcohol and methyl tert-butyl ether or in a mixture acetone/water allows preparing cis-clomiphene citrate as crystalline form VI.

Attempts to crystallize isomerically pure cis-clomiphene citrate as crystalline form I or VI in solvents such as ethanol, ethyl acetate, methylisobutylketone and 1,2-dichloromethane have failed.

It was also surprisingly found that for crystalline form I of cis-clomiphene citrate can be converted to crystalline form VI of cis-clomiphene citrate when crystalline form I of cis-clomiphene citrate is dissolved and reacted in a mixture comprising water and acetone.

The present invention is also directed to a process for preparing cis-clomiphene citrate as crystalline form I, which comprises the step of crystallizing cis-clomiphene citrate, such as isomerically pure cis-clomiphene citrate, in acetone.

The present invention is also directed to a process for preparing cis-clomiphene citrate as crystalline form VI, which comprises the step of crystallizing cis-clomiphene citrate, such as isomerically pure cis-clomiphene citrate, in a solvent selected from the group consisting of butan-2-ol, methanol, isopropyl alcohol and methyl tert-butyl ether or in a mixture acetone/water. In the mixture acetone/water, the water content may range from 2 to 5% in volume.

In some embodiments, the process disclosed herein for preparing isomerically pure cis-clomiphene citrate comprises, as step (e), the step of reacting citric acid with isomerically pure cis-clomiphene free base in acetone to convert isomerically pure cis-clomiphene free base to isomerically pure cis-clomiphene citrate as crystalline form I.

In some embodiments, the process disclosed herein for preparing isomerically pure cis-clomiphene citrate comprises, as step (e), the step of reacting citric acid with isomerically pure cis-clomiphene free base in a solvent selected from the group consisting of butan-2-ol, methanol, isopropyl alcohol and methyl tert-butyl ether or in a mixture acetone/water to convert isomerically pure cis-clomiphene free base to isomerically pure cis-clomiphene citrate as crystalline form VI.

In some embodiments, the process disclosed herein for preparing isomerically pure cis-clomiphene citrate further comprise the step of crystallizing isomerically pure cis-clomiphene citrate obtained in step (e) in acetone to obtain isomerically pure cis-clomiphene citrate as crystalline form I (step (f)).

In some embodiments, the process disclosed herein for preparing isomerically pure cis-clomiphene citrate further comprise the step of crystallizing isomerically pure cis-clomiphene citrate obtained in step (e) in a solvent selected from the group consisting of butan-2-ol, methanol, isopropyl alcohol and methyl tert-butyl ether or in a mixture acetone/water to obtain isomerically pure cis-clomiphene citrate as crystalline form VI (step (f)).

Preparation of cis-clomiphene citrate as crystalline form I or VI may be performed by reacting citric acid with isomerically pure cis-clomiphene free base in respectively acetone to obtain more particularly crystalline form I, or in a solvent selected from the group consisting of butan-2-ol, methanol, isopropyl alcohol and methyl tert-butyl ether or in a mixture acetone/water to obtain more particularly crystalline form VI. Isomerically pure cis-clomiphene may be obtained by the process herein disclosed. Citric acid is typically added gradually to the slurry, preferably at a temperature below the boiling point of the organic solvent, typically at a temperature ranging from about 45° C. to about 50° C., preferably at about 50° C. Citric acid may be gradually added over a period of 30 minutes to 6 hours. In some embodiments, the period is about 5 hours. The slurry, which may be seeded with isomerically pure cis-clomiphene citrate, is then allowed to cool to room temperature, i.e. 20° C. to 25° C., thereby causing isomerically pure cis-clomiphene citrate to crystallize and precipitate as crystalline form I or VI depending on the solvent.

Preparation of cis-clomiphene citrate as crystalline form I or VI may alternatively be performed by crystallizing isomerically pure cis-clomiphene citrate in respectively acetone to obtain more particularly crystalline form I or in a solvent selected from the group consisting of butan-2-ol, methanol, isopropyl alcohol and methyl tert-butyl ether or in a mixture acetone/water to obtain more particularly crystalline form VI. Isomerically pure cis-clomiphene may be obtained by the process herein disclosed. Recrystallization may be performed by methods known to the skilled person.

The present invention is also directed to a process for converting crystalline form I of cis-clomiphene citrate to crystalline form VI of cis-clomiphene citrate which comprises the step of adding crystalline form I of cis-clomiphene citrate in a mixture consisting of acetone and water to obtain a slurry, heating the slurry at a temperature ranging from about 40 to 55° C., preferably at about 50° C., typically for one to 10 days, preferably for about 5 days, and collecting cis-clomiphene citrate as crystalline form VI. Typically, the mixture comprises 2 to 5 vol. % of water, the remaining vol. % being acetone. Crystalline form I of cis-clomiphene citrate for use in said process may be obtained by the process herein disclosed.

The above disclosed processes are suitable for producing isomerically enriched and isomerically pure cis-clomiphene and any salts thereof at industrial scale.

Embodiments of the present invention will now be described by way of the following examples which are provided for illustrative purposes only, and not intended to limit the scope of the disclosure.

EXAMPLES

As used below, "Z" refers to the cis isomer of clomiphene (zuclomiphene or cis-clomiphene).

As used below "E" refers to the trans isomer of clomiphene.

Example 1: Production of Isomerically Enriched Cis-Clomiphene

To a 500 mL double jacketed reactor were introduced 35 g of clomiphene hydrobromide (0.07 mol, Z/E 30/70) and 140 mL of hydrobromic acid (HBr) 48% (4 volumes). The resulting mixture was stirred at 70° C. until having Z/E>50/50 (Z/E 51.1/48.9 after 20 h). The reactional mixture was then cooled down to 25° C., and 249 mL of a 5M NaOH solution (1 equiv. relative to the HBr) was added dropwise in 1 hour. A white gum appeared at the end of the addition. 200 mL of ethyl acetate were added and the solution was stirred until dissolution of the gum. The phases were separated, and aqueous layers were extracted with 2*100 mL of ethyl acetate. Combined organic layers were washed with 3*200 mL of water, until the washing water pH reach 7, and concentrated in vacuo in order to give the clomiphene free base (Z/E 51.6/48.4, 28 g, 100%) as a yellowish viscous oil.

Example 1 A: Not According to the Present Invention

A suspension of 200 mg of clomiphene hydrobromide (Z/E 30/70) in 0.8 mL of HBr 48% (4 volumes) and 0.8 mL of ethyl acetate was heated to 70° C. After 16 h, the ratio Z/E was 34/66.

Example 1 B: Not According to the Present Invention

A solution of 10 g of clomiphene hydrobromide (Z/E 26/74) in 30 mL of HBr 48% (3 volumes) and 30 mL of n-butanol was heated to 55° C. After 21 h, the ratio Z/E was 27/73.

Example 2: Isolation Via Crystallization of Isomerically Pure Cis-Clomiphene Hydrobromide To a 500 mL double jacketed reactor was introduced a solution of clomiphene free base (28 g, 0.07 mol, Z/E 51.6/48.4) in acetone (280 mL, 10 vol.). Clomiphene free base was prepared in accordance with example 1. The mixture was heated up to 25° C. and 7.92 mL of HBr 48% (1 equiv., 0.07 mol) were added dropwise for 30 min at 25° C. Once the addition completed, the mixture was heated up to 50° C. Once this temperature reached, the mixture was seeded with 300 mg of cis-clomiphene hydrobromide (1%). Stirring was then maintained 1 h at 50° C., and the mixture was cooled back to 25° C. in 5 h, and maintained at 25° C. for 16 h. The newly formed solid was filtrated and washed with 2*66 mL of acetone (2*2 vol), and was dried in the oven at 40° C. under reduced pressure for 3 h to give cis-clomiphene hydrobromide (11.4 g, 33%, Z/E 98.15/1.85) as a white solid.

Example 2a (not According to the Present Invention)

To a solution of 2.7 g of clomiphene base in 15 mL of isopropanol was added 1 eq of HBr 48%. The mixture was heated to 50° C., kept at this temperature over 1 h then cooled to 30° C. Seeds were added. After 1 h, the formed solid was collected by filtration washed with isopropanol and dried. The ratio Z/E of the isolated solid was 64/36.

Example 3: Isolation Via Crystallization of Isomerically Pure Cis-Clomiphene Hydrobromide To a 5 L jacketed reactor was introduced clomiphene free base Z/E 55.4/44.6 (155 g, 0.38 mol) in acetone (1.55 mL, 10 vol). Hydrobromic acid 48% (43.2 mL, 1 eq.) was added to the mixture dropwise at 25° C. The mixture was then heated up to 50° C. and seeded with cis-clomiphene hydrobromide. Stirring was then maintained 1 h at 50° C., and the mixture was cooled down to 25° C. in 3 h and maintained at 25° C. overnight. The newly formed solid was filtrated and washed with 2×250 mL of acetone was dried in the oven at 40° C. under reduced pressure to give cis-clomiphene hydrobromide (77.2 g, Z/E 97.85/2.15) as a white solid.

Example 4: Preparation of Isomerically Pure Cis-Clomiphene Free Base

To a solution of 261.8 g of clomiphene free base Z/E 61.5/38.5 in 2.6 L of acetone, 73 mL of hydrobromic acid 48% were added to the mixture dropwise at 25° C. The mixture was then heated up to 50° C. and seeded with clomiphene hydrobromide. Stirring was then maintained 1 h at 50° C., and the mixture was cooled down to 25° C. in 3 h and maintained at 25° C. overnight. The newly formed solid was filtrated and washed with 2×250 mL of acetone. The wet cis-clomiphene hydrobromide obtained (Z/E 97.04/2.96) was added to 525 mL of water, 525 mL of ethyl acetate and 160 mL of NaOH 20%. When complete solubilization was obtained, the aqueous phase was removed and the organic phase was washed twice with 250 mL of water and then concentrated to dryness. 127.7 g of cis-clomiphene free base were obtained with an overall yield of 48.8%.

Example 5: Preparation of Isomerically Pure Cis-Clomiphene Hydrobromide

To a solution of 25.5 kg of clomiphene free base (Z/E 44/55) in 255 L of acetone, 10.6 kg of hydrobromic acid 48% were added to the mixture dropwise at 25° C. The mixture was then heated up to 50° C. and seeded with clomiphene hydrobromide. Stirring was then maintained 1 h at 50° C., and the mixture was cooled down to 25° C. in 3 h and maintained at 25° C. overnight. The newly formed solid was filtrated and washed with 2×26 L of acetone. 15.5 kg of cis-clomiphene hydrobromide containing 22.26% of acetone were isolated (38.5%, Z/E 98/2).

Example 6: Preparation of Isomerically Pure Cis-Clomiphene Citrate

To a 500 mL jacketed reactor was introduced cis-clomiphene hydrobromide (24.98 g, 0.05 mol) in ethyl acetate (95 mL, 3.70 vol.) and water (95 mL, 3.70 vol.). NaOH 20% w/w was added. (25 mL, 3 eq.). After stirring, the phases were separated. The organic layer was washed with 50 mL of water, until the washing water pH was below 8. Ethyl acetate was eliminated by concentration in vacuo and replaced by acetone (156 mL, 7.5 vol) and water (4.2 mL, 0.17 vol). The mixture was heated up to 50° C. and a solution of citric acid (9.86 g, 51.31 mol) in acetone (52 mL, 2.5 vol.) was added over 5 h. The mixture was seeded with 20 mg of cis-clomiphene citrate. Stirring was then maintained 4 h at 50° C., and the mixture was cooled down to 20° C. in 3 h and maintained at 20° C. overnight. The newly formed solid was filtrated and washed with 40 mL of acetone and was dried in the oven at 40° C. under reduced pressure to give cis-clomiphene citrate (27.7 g, 90%, Z/E 99.48/0.52) as a white solid.

Example 7: Preparation of Cis-Clomiphene Citrate as Crystalline Form I

To a solution of 135.34 g of cis-clomiphene free base in 1000 mL of acetone heated to 50° C., 64.05 g of citric acid solubilized in 340 mL of acetone at about 50° C. is added over 30 min. The mixture is maintained at about 50° C. for about 1 hour, then cooled to about 20° C. and maintained for about 2 hours at this temperature. The crystallized product is isolated by filtration and washed with 270 mL of acetone. The product is dried under vacuum at about 50° C. The product is delumped. The product is obtained with a 93% yield. XRPD of the obtained product corresponds to cis-clomiphene citrate form I.

Example 8: Preparation of Cis-Clomiphene Citrate as Crystalline Form VI

Example 8A: Acetone/Water as Solvent

A suspension of 3.1 g of cis-clomiphene citrate in 20.6 mL of acetone and 1.1 mL of water is heated at 50° C. for 4 h. Then the suspension is cooled to room temperature and kept overnight at this temperature. The solid is isolated by filtration and dried under vacuum at about 40° C.

XRPD of the obtained product corresponds to cis-clomiphene citrate form VI.

The cis-clomiphene citrate form VI is obtained with an 83.9% yield.

Example 8B: Butan-2-Ol as Solvent 50 mg of cis-clomiphene free base is solubilized in 0.25 mL of 2-butanol at 50° C. 1.1 eq of citric acid solubilized in butan-2-ol (1.3 mol/L) is added and the reaction mixture is kept at 50° C. for 16 h. The solid obtained is then collected by filtration and washed.

XRPD of the obtained product corresponds to cis-clomiphene citrate form VI.

Example 8C: Methyl Tert-Butyl Ether as Solvent

The procedure of example 8b was applied with butan-2-ol being replaced with methyl tert-butyl ether.

XRPD of the obtained product corresponds to cis-clomiphene citrate form VI.

Example 8D: Isopropyl Alcohol as Solvent

The procedure of example 8b was applied with butan-2-ol being replaced with isopropyl alcohol.

XRPD of the obtained product corresponds to cis-clomiphene citrate form VI.

Example 2E: Methanol as Solvent

A suspension of 150 mg of cis-clomiphene citrate in 0.75 mL of methanol is heated to reflux. When the solubilization is completed, the mixture is cooled to room temperature. The crystallized product is isolated by filtration and washed with 0.15 mL of methanol. The product is dried under vacuum at about 40° C.

XRPD of the obtained product corresponds to cis clomiphene citrate form VI.

Example 9: Conversion of Crystalline Form I of Cis-Clomiphene Citrate to Crystalline Form VI of Cis-Clomiphene Citrate A suspension of 0.270 g of cis-clomiphene Form I in 2.67 mL of acetone and 0.03 mL of water was heated to 50° C. After 5 days at 50° C., XRPD showed a complete transition of cis-clomiphene form I to form VI.

Example 9A: Not According to the Present Invention

A suspension of 0.240 g of cis-clomiphene Form I in 2.4 mL of acetone was heated to 50° C. After 5 days at 50° C., XRPD showed that no pure crystal form was observed but rather a mixture of crystal forms.

The invention claimed is:

1. A process for the production of isomerically enriched cis-clomiphene free base or a salt thereof from isomerically pure or isomerically enriched trans-clomiphene hydrobromide comprising:
    (a) reacting hydrobromic acid with the isomerically pure or isomerically enriched trans-clomiphene hydrobromide in the absence of organic solvent to provide isomerically enriched cis-clomiphene hydrobromide, and
    (b) optionally converting the isomerically enriched cis-clomiphene hydrobromide to isomerically enriched cis-clomiphene free base or a salt thereof other than hydrobromide.

2. The process according to claim 1 wherein the isomerically enriched cis-clomiphene free base or a salt thereof is isomerically pure cis-clomiphene free base or salt thereof, the process further comprising:
    (b) converting the isomerically enriched cis-clomiphene hydrobromide obtained in step (a) to an isomerically enriched cis-clomiphene free base;
    (c) reacting hydrobromic acid with the isomerically enriched cis-clomiphene free base obtained in step (b) in acetone to selectively crystallize isomerically pure cis-clomiphene hydrobromide;
    (d) optionally converting the isomerically pure cis-clomiphene hydrobromide obtained in step (c) to isomerically pure cis-clomiphene free base;
    (e) optionally converting the isomerically pure cis-clomiphene hydrobromide obtained in step (c) or the isomerically pure cis-clomiphene free base obtained in step (d) to an isomerically pure cis-clomiphene salt other than the isomerically pure cis-clomiphene hydrobromide.

3. The process according to claim 2 for preparing isomerically pure cis-clomiphene citrate comprising:
    (a) reacting hydrobromic acid with isomerically pure or isomerically enriched trans-clomiphene hydrobromide in the absence of organic solvent to provide isomerically enriched cis-clomiphene hydrobromide;
    (b) converting the isomerically enriched cis-clomiphene hydrobromide obtained in step (a) to an isomerically enriched cis-clomiphene free base;
    (c) reacting hydrobromic acid with the isomerically enriched cis-clomiphene free base obtained in step (b) in acetone to selectively crystallize isomerically pure cis-clomiphene hydrobromide;
    (d) converting the isomerically pure cis-clomiphene hydrobromide obtained in step (c) in isomerically pure cis-clomiphene free base;
    (e) converting the isomerically pure cis-clomiphene free base obtained in step (d) to isomerically pure cis-clomiphene citrate.

4. The process according to claim 3 wherein step (d) is performed by reacting the isomerically pure cis-clomiphene hydrobromide with a base.

5. The process according to claim 3 wherein step (e) is performed by reacting citric acid with isomerically pure cis-clomiphene free base.

6. The process according to claim 2 wherein step (c) is performed by reacting from 0.9 to 1.2 equivalents, of hydrobromic acid relative to isomerically enriched cis-clomiphene free base.

7. The process according to claim 1 wherein step (a) is performed at a temperature ranging from about 45 to about 80° C.

8. The process according to claim 1 wherein step (a) is performed by reacting from four to ten volumes of hydrobromic acid relative to the isomerically pure or isomerically enriched trans-clomiphene hydrobromide.

9. The process according to claim 3 wherein step (c) is performed by reacting from 0.9 to 1.2 equivalents of hydrobromic acid relative to isomerically enriched cis-clomiphene free base.

10. The process according to claim 2 wherein step (a) is performed at a temperature ranging from about 45 to about 80° C.

11. The process according to claim 3 wherein step (a) is performed at a temperature ranging from about 45 to about 80° C.

12. The process according to claim 2 wherein step (a) is performed by reacting four to ten volumes of hydrobromic acid relative to the isomerically pure or isomerically enriched trans-clomiphene hydrobromide.

13. The process according to claim 3 wherein step (a) is performed by reacting from four to ten volumes of hydrobromic acid relative to the isomerically pure or isomerically enriched trans-clomiphene hydrobromide.

14. The process according to claim 3 wherein step (d) is performed by reacting the isomerically pure cis-clomiphene hydrobromide with a base in a mixture comprising an organic solvent and water.

15. The process according to claim 3 wherein step (e) is performed by reacting citric acid with isomerically pure cis-clomiphene free base in acetone.

16. The process according to claim 1 wherein step (a) is performed at about 70° C.

17. The process according to claim 2 wherein step (c) is performed by reacting one equivalent of hydrobromic acid relative to isomerically enriched cis-clomiphene free base.

\* \* \* \* \*